United States Patent
Vadlamani et al.

(10) Patent No.: US 10,344,069 B2
(45) Date of Patent: Jul. 9, 2019

(54) PROCESS FOR THE PREPARATION OF LIRAGLUTIDE

(71) Applicants: Auro Peptides Ltd, Hyderabad, Telangana (IN); Suresh Kumar Vadlamani, Hyderabad (IN); Patil Nilesh Dagadu, Hyderabad (IN); Mohammed Abdul Shafee, Hyderabad (IN); Sanjay Devidas Patil, Hyderabad (IN); Nagana Goud Agasaladinni, Hyderabad (IN)

(72) Inventors: Suresh Kumar Vadlamani, Hyderabad (IN); Patil Nilesh Dagadu, Hyderabad (IN); Mohammed Abdul Shafee, Hyderabad (IN); Sanjay Devidas Patil, Hyderabad (IN); Nagana Goud Agasaladinni, Hyderabad (IN)

(73) Assignee: Auro Peptides Ltd., Hyderabad (IN)

( * ) Notice: Subject to any disclaimer, the term of this patent is extended or adjusted under 35 U.S.C. 154(b) by 0 days.

(21) Appl. No.: 15/523,384

(22) PCT Filed: Oct. 31, 2015

(86) PCT No.: PCT/IB2015/058429
§ 371 (c)(1),
(2) Date: Apr. 29, 2017

(87) PCT Pub. No.: WO2016/067271
PCT Pub. Date: May 6, 2016

(65) Prior Publication Data
US 2018/0251511 A1 Sep. 6, 2018

(30) Foreign Application Priority Data

Oct. 31, 2014 (IN) .......................... 5472/CHE/2014

(51) Int. Cl.
*C07K 14/605* (2006.01)
(52) U.S. Cl.
CPC ................................. *C07K 14/605* (2013.01)
(58) Field of Classification Search
CPC .......... A61K 38/00; A61K 2039/55516; A61L 27/54
See application file for complete search history.

(56) References Cited

U.S. PATENT DOCUMENTS 9,260,474 B2 * 2/2016 Pan ...................... C07K 14/605
2002/0177725 A1 * 11/2002 Priestley ................ C07F 5/025
558/288

FOREIGN PATENT DOCUMENTS

WO WO-2013037266 A1 * 3/2013 ............... C07K 1/14

* cited by examiner

*Primary Examiner* — Marcela M Cordero Garcia
*Assistant Examiner* — Jia-Hai Lee
(74) *Attorney, Agent, or Firm* — Jay R Akhave (57) ABSTRACT

The present invention relates to a process for the preparation of Liraglutide, which comprises: a) synthesis of suitable fragments (protected) by solid phase peptide synthesis; b) coupling of the suitable fragments on solid support; c) concurrently cleaving the protected peptide from the solid support and de-protecting the peptide; d) purification of Liraglutide (crude) on reverse phase HPLC; e) isolating pure Liraglutide.

15 Claims, 4 Drawing Sheets

Specification includes a Sequence Listing.

PROCESS FOR THE PREPARATION OF LIRAGLUTIDE

FIELD OF THE INVENTION

The present invention relates to a process for the preparation of Liraglutide of Formula I.

His-Ala-Glu-Gly-Thr-Phe-Thr-Ser-Asp-Val-Ser-Ser-Tyr-Leu-Glu-Gly-Gln-Ala-Ala-Lys-Glu-Phe-
Ile-Ala-Trp-Leu-Val-Arg-Gly-Arg-Gly-OH

Formula I

BACKGROUND OF THE INVENTION

Liraglutide is an acylated human glucagon-like peptide-1 (GLP-1) agonist, with a 97% amino acid sequence identity to endogenous human GLP-1(7-37). GLP-1(7-37) represents less than 20% of total circulating endogenous GLP-1. Like GLP-1(7-37), Liraglutide activates the GLP-1 receptor, a membrane-bound cell-surface receptor coupled to adenylyl cyclase by the stimulatory G-protein, Gs, in pancreatic beta cells.

Liraglutide increases intracellular cyclic AMP (cAMP), leading to insulin release in the presence of elevated glucose concentrations. This insulin secretion subsides as blood glucose concentrations decrease and approach euglycemia. Liraglutide also decreases glucagon secretion in a glucose-dependent manner. The mechanism of blood glucose lowering also involves a delay in gastric emptying. GLP-1(7-37) has a half-life of 1.5-2 minutes due to degradation by the ubiquitous endogenous enzymes, dipeptidyl peptidase IV (DPP-IV) and neutral endopeptidases (NEP). Unlike native GLP-1, Liraglutide is stable against metabolic degradation by both peptidases and has a plasma half-life of 13 hours after subcutaneous administration. The pharmacokinetic profile of Liraglutide, which makes it suitable for once daily administration, is a result of self-association that delays absorption, plasma protein binding and stability against metabolic degradation by DPP-IV and NEP.

Liraglutide is marketed in USA under the trade name Victoza® in the form of injection and supplied in multiple dose pre-filled pen injectors. Liraglutide is indicated as an adjunct to diet and exercise to achieve glycemic control in patients with type 2 diabetes mellitus.

Liraglutide for first time disclosed in U.S. Pat. No. 6,268,343. In this patent, Liraglutide precursor is produced by recombinant DNA technology from yeast *Sachromyces Cerevisiae* and further chemically modified by an addition of a Glu-spaced hexadecanoic (palmitic) acid using solution phase method to produce Liraglutide.

The disadvantage of the above process is the N-terminal of GLP-1(7-37)-OH is not protected, which leads to generation of impurities. Additional purification steps are required to remove these impurities, and makes Liraglutide high cost and not suitable for large scale production.

WO 2013/037266 discloses a process to prepare Liraglutide by solid phase synthesis, following sequential addition of amino acids to the supported resin (Wang or 2-chlorotrityl resin) and thereafter cleaved from resin and de-protection is carried out in two steps.

The disadvantage of the above process is, it leads to impure, crude Liraglutide and it is difficult to purify.

CN 102875665 discloses a process for the preparation of Liraglutide by Fragment coupling. Process of CN '665 involves the use of peptide fragment: Fmoc-Gln(Trt)-Ala-Ala-Lys(N-ε-(Na-Palmitoyl-L-γ-glutamyl-OtBu))-Glu (OtBu)-Phe-Ile-Ala-OH in the synthesis of Liraglutide.

The disadvantage of the above process is, it leads to formation of optically impure Liraglutide and it is difficult to purify to its homogeneity.

CN 103145828 discloses a process to prepare Liraglutide by solid phase synthesis, following sequential addition of amino acids to the supported resin.

The disadvantage of the above process is, it leads to impure, crude Liraglutide and it is difficult to purify.

The present inventors have made Liraglutide by the process, which is supposed to be simple and industrially scalable with consistent yields. Further, the Liraglutide obtained by the process of the present invention results in higher yield and purity.

The present invention relates to a process for the preparation of Liraglutide by using two or more suitable fragments (protected) by solid phase peptide synthesis, coupling of the fragments on solid support, concurrent cleavage from the solid support and deprotection of peptide, purification of Liraglutide (crude) on reverse phase HPLC, freeze-drying and isolation of pure Liraglutide.

The use of two or more fragments for preparing Liraglutide according to the present invention leads to a better purity product with low level of impurities.

OBJECTIVE OF INVENTION

An objective of the present invention is to provide a process for preparing Liraglutide, which is simple, industrially applicable and robust.

Another objective of the present invention is to provide a process for preparing Liraglutide, which yields high purity product.

Yet another objective of the present invention is to provide a process for preparing Liraglutide, which results in consistent yields.

SUMMARY OF THE INVENTION

The present invention relates to a process for the preparation of Liraglutide of formula I, Formula I which comprises the following steps:
a) Synthesis of suitable fragments (protected) by solid phase peptide synthesis;

```
Y-Thr(X)-Phe-Thr(X)-Ser(X)-Asp(X)-Val-Ser(X)-

Ser(X)-Tyr(X)-Leu-Glu(X)-Gly-Gln(Trt)-Ala-Ala-Lys-

ϵ(P)-Glu(X)-Phe-Ile-Ala-Trp(X)-Leu-Val-Arg(Z)-Gly-

Arg(Z)-Gly-Resin Fragment A

Boc-His (Trt)-Ala-Glu(X)-Gly-OH Fragment B

Y-Gln(Trt)-Ala-Ala-Lys-ϵ(P)-Glu(X)-Phe-Ile-Ala-

Trp(X)-Leu-Val-Arg(Z)-Gly-Arg((Z)-Gly-Resin

Fragment C

Y-Ser(X)-Tyr(X)-Leu-Glu(X)-Gly-OH Fragment D
``` b) coupling of the fragments on solid support;
c) concurrent cleavage from the solid support and deprotection of peptide;
d) purification of Liraglutide (crude) on reverse phase HPLC;
e) isolating pure Liraglutide.
wherein, Y represents amino protecting group, X represents carboxyl, phenol and alcoholic protecting group, Z represents guanidine protecting group and P represents amino protecting group of €-amino group of Lys.

BRIEF DESCRIPTION OF ABBREVIATIONS

Palmitoyl—hexadecanoyl
DMF—N,N-dimethylformamide
DCM—Dichloromethane
THF—Tetrahydrofuran
NMP—N-Methyl pyrrolidine
DMAC—Dimethylacetamide
TFA—Trifluoro acetic acid
TIPS—Triisopropyl silane
TIS—Triisopropyl silane
DTT—Diothreitol
DMS—Dimethyl sulfide
CTC—Chlorotrityl chloride
Trt—Trityl
Fmoc—9-fluorenylmethoxycarbonyl
Boc—tert-butoxycarbonyl
X=Boc (t-butoxycarbonyl)—or t'But, Trt, DMT-dimethoxy trityl and MMT-Methoxytrityl
Y=Fmoc—9-fluorenylmethoxycarbonyl, Boc-tert-butoxycarbonyl, Cbz—benzyloxycarbonyl or Bpoc—2-(4-biphenyl)-2-propyloxycarbonyl
Z=Pbf (pentamethyldihydrobenzofurane-5-sulfonyl), Pmc (2,2,5,7,8-pentamethylchroman-6-sulfonyl).
P=IVDde (4,4-Dimethl-2,6-dioxocyclo-hex-1-ylidene-3methylbutyl), Dde [1-(4,4-dimethyl-2,6-dioxycyclohex-1-ylidine)ethyl], Aloc (allyloxycarbonyl), Mtt(4-methyltrityl), Cbz (benzyloxycarbonyl) and Boc.

DETAILED DESCRIPTION OF THE INVENTION

The present invention relates to a process for the preparation of Liraglutide by coupling of two or more suitable protected fragments on solid support.
In yet another embodiment of the present invention, the suitable fragments selected for the preparation of Liraglutide are as follows:

```
Y-Thr(X)-Phe-Thr(X)-Ser(X)-Asp(X)-Val-Ser(X)-

Ser(X)-Tyr(X)-Leu-Glu(X)-Gly-Gln(Trt)-Ala-Ala-Lys-

ϵ(P)-Glu(X)-Phe-Ile-Ala-Trp(X)-Leu-Val-Arg(Z)-Gly-

Arg(Z)-Gly-Resin Fragment A

Boc-His (Trt)-Ala-Glu(X)-Gly-OH Fragment B

Y-Gln(Trt)-Ala-Ala-Lys-ϵ(P)-Glu(X)-Phe-Ile-Ala-

Trp(X)-Leu-Val-Arg(Z)-Gly-Arg((Z)-Gly-Resin

Fragment C

Y-Ser(X)-Tyr(X)-Leu-Glu(X)-Gly-OH Fragment D
``` wherein, Y represents amino protecting group, X represents carboxyl, phenol and alcoholic protecting group, Z represents guanidine protecting group and P represents amino protecting group of €-amino group of Lys.

In yet another embodiment of the present invention, the amino protecting groups are selected from but not limited to a group comprising of Fmoc, Boc, Cbz, Bpoc, and the like.

In yet another embodiment of the present invention the carboxyl, phenolic and alcoholic groups are protected with groups selected from but not limited to a group comprising of DMT, MMT, Trt, tert-butyl, t-butoxy carbonyl, and the like.

In yet another embodiment of the present invention, the guanidine protecting groups are selected from but not limited to a group comprising of Pbf and Pmc.

In yet another embodiment of the present invention, the amino protecting groups of €-amino group of Lys at position 20 are selected from but not limited to a group comprising of IVDde, Dde, Aloc, Mtt, Cbz and Boc.

In another embodiment of the present invention, the coupling agents are selected from the group comprising of hydroxybenzotriazole (HOBt); O-(7-azabenzotriazol-1-yl)-1,1,3,3-tetramethyluronium hexafluorophosphate (HATU), O-(benzotriazol-1-yl)-N,N,N',N'-tetramethyluronium tetrafluoroborate (TBTU), 1,3-dicyclohexylcarbodiimide (DCC), 1-(dimethylaminopropyl)-3-ethylcarbodiimide hydrochloride (EDC HCl), diisopropylcarbodiimide (DIC), isopropylchloroformate (IPCF), O-(benzotriazol-1-yl)-1,1,3,3-tetramethyluronium hexafluorophosphate (HBTU), benzotriazol-1-yl-oxy-tris(dimethyl-amino)-phosphonium hexafluorophosphate (BOP), N,N-bis-(2-oxo-3-oxazolidinyl)phosphonic dichloride (BOP—Cl), benzotriazol-1-yloxytri(pyrrolidino)phosphonium hexafluorophosphate (PyBOP), bromotri(pyrrolidino)phosphonium hexafluorophosphate (PyBrOP), chlorotri(pyrrolidino)phosphonium hexafluorophosphate (PyClOP), ethyl-2-cyano-2-(hydroxyimino) acetate (Oxyma Pure), O-(6-Chloro-1-hydrocibenzotriazol-1-yl)-1,1,3,3-tetramethyluronium tetrafluoroborate (TCTU), 2-(5-norbornen-2,3-dicarboximido)-1,1,3,3-tetramethyluronium tetrafluoroborate (TNTU), propane phosphonic acid anhydride (PPAA), 2-succinimido-1,1,3,3-tetramethyluronium tetrafluoro borate (TSTU), bromo-tris-pyrrolidino-phosphonium hexafluorophosphate (PyBroP), iso-butylchloroformate (IBCF), Ethyl 1,2-dihydro-2-ethoxyquinoline-1-carboxylate (EEDQ), 1-Cyano-2-ethoxy-2-oxoethylidenaminooxy)dimethylamino-morpholino-carbenium hexafluorophosphate (COMU), 3-(diethoxyphosphoryloxy)-1,2,3-benzotriazin-4(3H)-one (DEPBT) or mixtures thereof.

In another embodiment of the present invention the coupling takes place in one of the solvents selected from the group comprising of DMF, DCM, THF, NMP, DMAC methanol, ethanol, isopropanol, dichloroethane, 1,4-dioxane, 2-methyl tetrahydrofuran ethyl acetate, acetonitrile, acetone, and the like or a mixture of the listed solvents.

In still another embodiment of the present invention, the coupling reaction is carried out in presence of a base. The base is organic or inorganic base. The inorganic base is selected from the group comprising of potassium carbonate, lithium carbonate, sodium carbonate, sodium ethoxide, sodium bicarbonate, potassium bicarbonate, sodium hydroxide, potassium hydroxide, ammonium hydroxide, and mixtures thereof; the organic base is selected from the group comprising of diisopropylamine, N,N-diisopropylethylamine triethylamine, dimethylamine, trimethyl amine, isopropyl ethylamine, pyridine, N-methyl morpholine and mixtures thereof.

In yet another embodiment of the present invention the solid phase synthesis is carried out on an insoluble polymer which is acid sensitive. Acid sensitive resin selected from the group comprising Chlorotrityl resin (CTC), Sasrin, Wang Resin, 4-methytrityl chloride, TentaGel S, TentaGel TGA, Rink acid resin, NovaSyn TGT resin, HMPB-AM resin, 4-(2-(amino methyl)-5-methoxy)phenoxy butyric acid anchored to polymeric resin MBHA, 4-(4-(amino methyl)-3-methoxy)phenoxy butyric acid anchored to polymeric resin MBHA and 4-(2-(amino methyl)-3,3-dimethoxy)phenoxy butyric acid anchored to polymeric resin MBHA include, most preferred super acid labile resin is 2-chlorotrityl resins.

In yet another embodiment of the present invention, the protected Liraglutide is de-protected with a mixture of reagents selected from the group comprising of TFA, TIS, TIPS, DTT, EDT, ammonium iodide, 2,2'-(ethylenedioxy) diethane and acetyl cystein, DMS, phenol, cresol and thiocresol.

In yet another embodiment of the present invention, the purification of Liraglutide is carried out by reverse phase HPLC using solvents: TFA in water, acetic acid, acetonitrile, orthophosphoric acid in water, triethylamine in water, ammonium acetate in water and ammonium bicarbonate in water.

In yet another embodiment of the present invention, the final isolation of Liraglutide is carried out by lyophilization.

In yet another embodiment of the present invention, a process for the preparation of Liraglutide comprising Fragment "A", wherein, Fragment A is prepared by solid phase peptide synthesis.

In yet another embodiment of the present invention, a process for the preparation of Liraglutide comprising Fragment "B", wherein, Fragment B is prepared by solid phase peptide synthesis.

In yet another embodiment of the present invention, a process for the preparation of Liraglutide comprising Fragment "C", wherein, Fragment C is prepared by solid phase peptide synthesis.

In yet another embodiment of the present invention, a process for the preparation of Liraglutide comprising Fragment "D", wherein, Fragment D is prepared by solid phase peptide synthesis.

In yet another embodiment of the present invention, a process for the preparation of Liraglutide precursor peptide on solid support by solid phase peptide synthesis is described:

```
Boc-His(Trt)-Ala-Glu(x)-Gly-Thr(X)-Phe-Thr(X)-

Ser(X)-Asp(X)-Val-Ser(X)-Ser(X)-Tyr(X)-Leu-Glu(X)-

Gly-Gln(Trt)-Ala-Ala-Lys-ϵ(P)-Glu(x)-Phe-Ile-Ala-

Trp(X)-Leu-Val-Arg(z)-Gly-Arg(z)-Gly-Resin
```

In another embodiment of the present invention, deblocking of amino protecting group on €-amino group of Lys at position 20 by hydrazine hydrate is described.

In another embodiment of the present invention, coupling of Palmtoyl-Glu-(α-t'Butyl')-γ-OH at the € amino group of Lys at position 20 is described.

In yet another embodiment of the present invention, cleavage and deblocking of Liraglutide from solid support is described.

Figure 1:
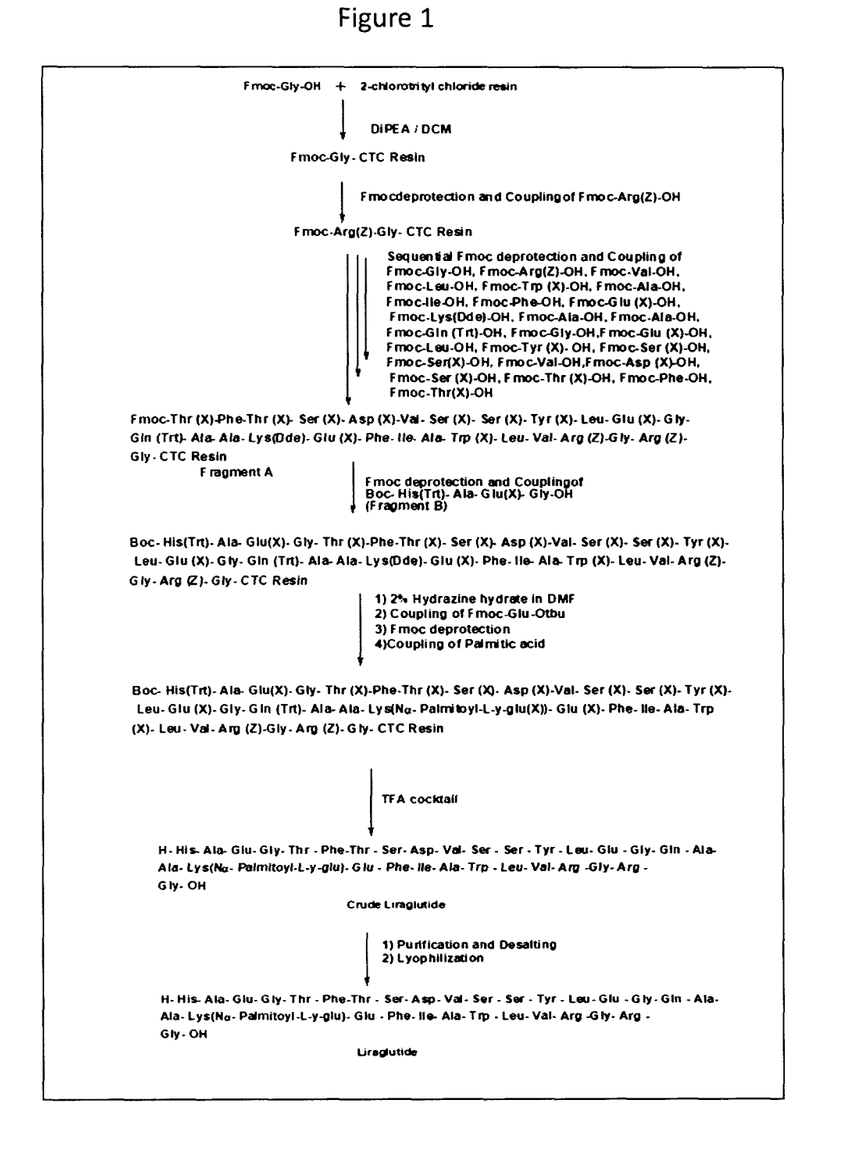
FIG. 1: Scheme for one embodiment of the process for the preparation of Liraglutide.

In yet another embodiment of the present invention, the process for the preparation of Liraglutide is shown in FIG. 1.

Figure 2:
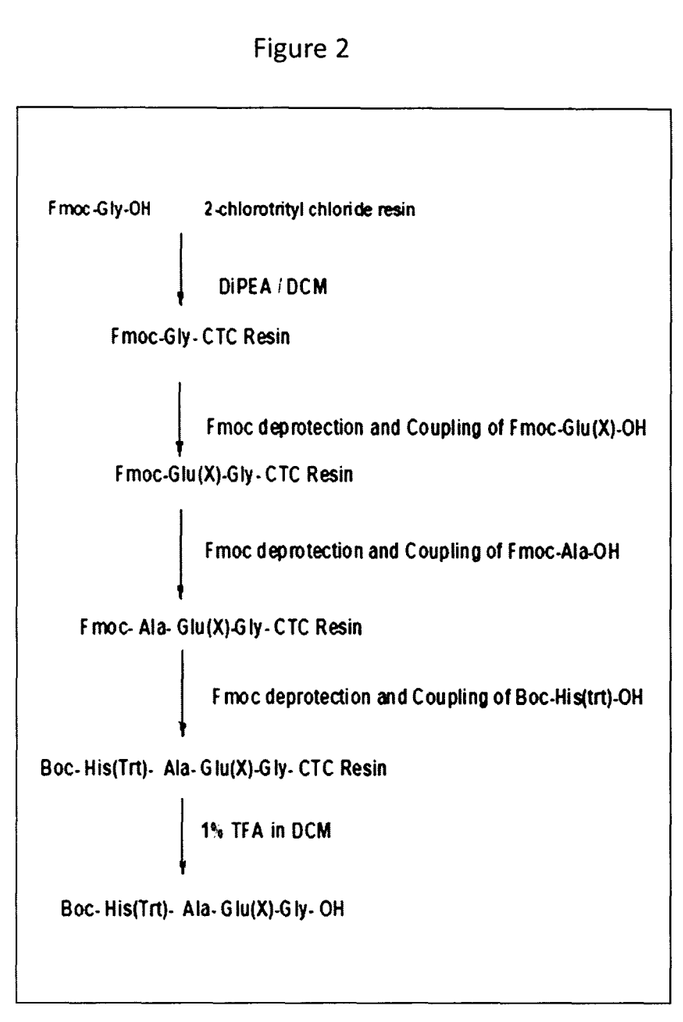
FIG. 2: Scheme for the process for the preparation of Fragment B.

In yet another embodiment of the present invention, the process for the preparation of Fragment B is shown in FIG. 2.

Figure 3:
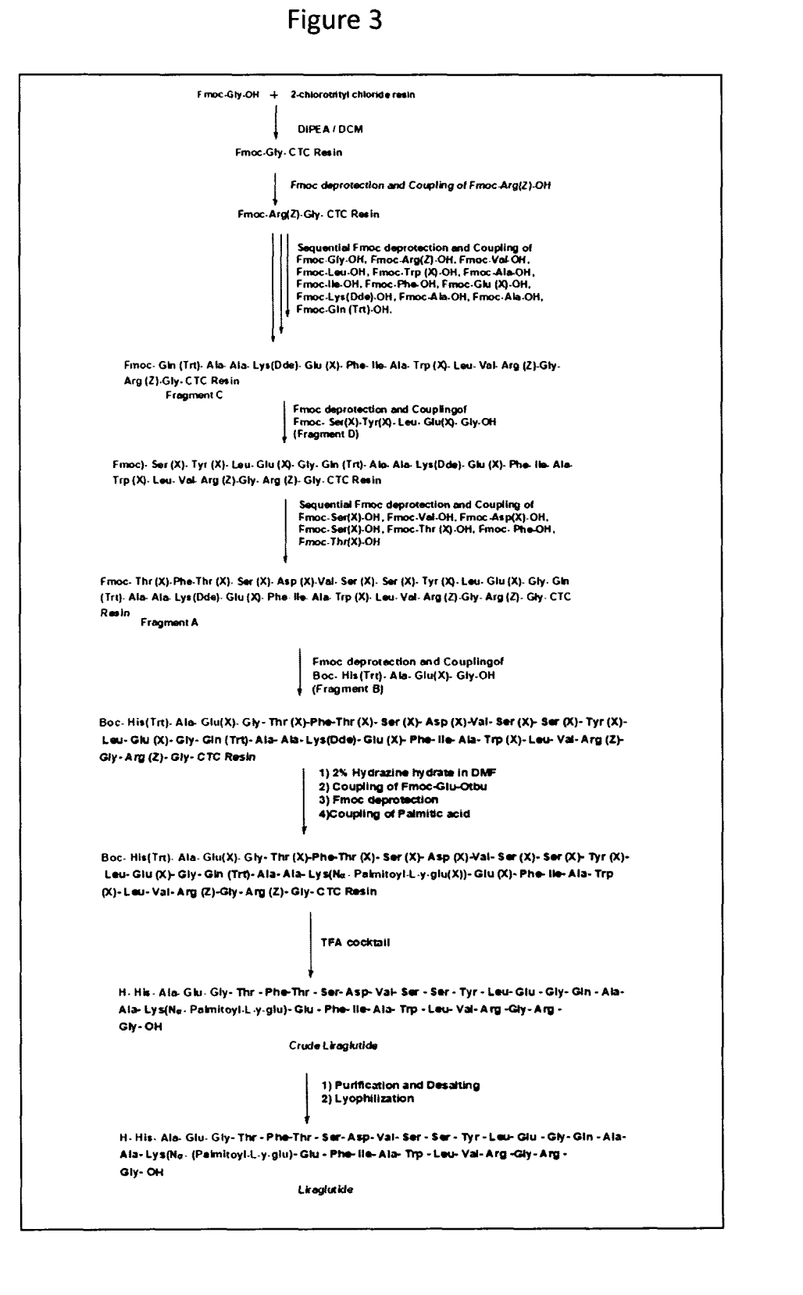
FIG. 3: Scheme for another embodiment of the process for the preparation of Liraglutide.

In yet another embodiment of the present invention, the process for the preparation of Liraglutide is shown in FIG. 3.

Figure 4:
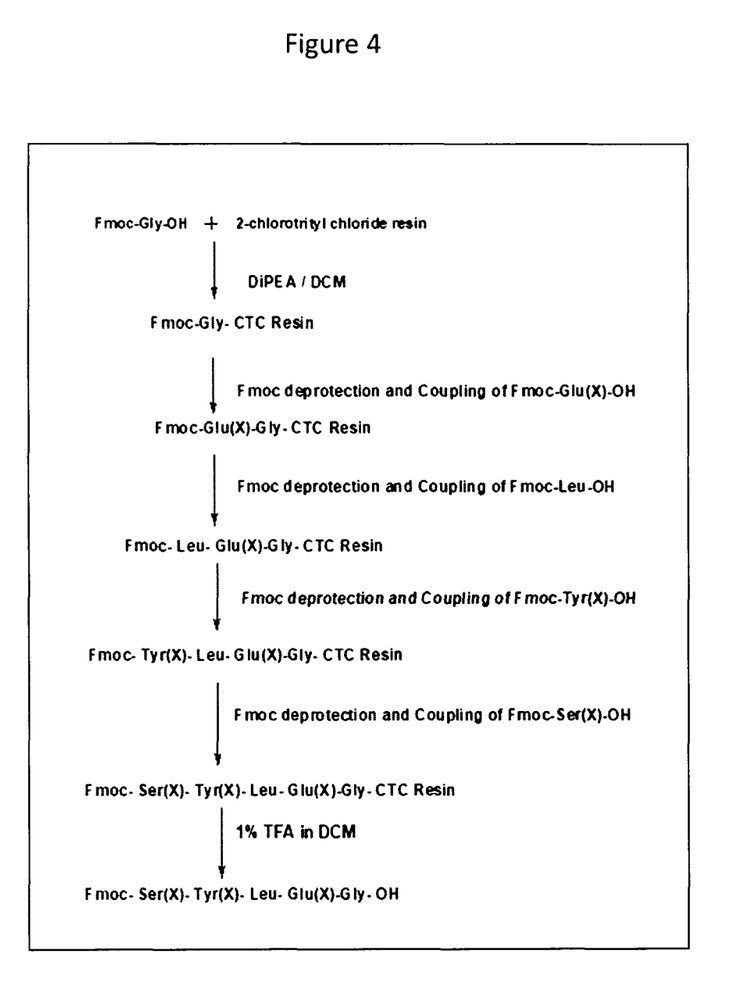
FIG. 4: Scheme for the process for the preparation of Fragment D.

In yet another embodiment of the present invention, the process for the preparation of Fragment D is shown in FIG. 4.

The invention is illustrated with the following examples, which are provided by way of illustration only and should not be construed to limit the scope of the invention in any manner whatsoever.

Example 1

Synthesis of Boc-His (Trt)-Ala-Glu (Otbu)-Gly-OH (Fragment B)

Step A

CTC resin (50 gm) was taken in a SPPS reactor, 500 ml of dry dichloromethane was added and allowed it to swell for 10 min and drained.

Step B

A solution of Fmoc-Gly-OH (45 gm, 2 eq) and DIEA (39.5 ml, 3 eq) in dry dichloromethane (500 ml) was added to the resin at step A and stirred for one to two hours at room temperature and drained. The resin was then capped with 400 ml of DIEA (1%) solution in DCM: Methanol (1:1)) for 20 min and drained. Thereafter, washed the resin with one bed volume of DMF (2 times), DCM (2 times) and MTBE (2 times) isolated and dried.

Yield: 79 gm
Loading ~0.92

The above resin was deblocked with 500 ml of 20% piperidine in DMF for 10 and 15 minutes and washed with 400 ml of DMF (2 times), IPA (2 times) and DMF (2 times).

Step C

Fmoc-Glu(Otbu)-OH (62 gm, 2 eq.) and HOBT (20 gm, 2 eq) were dissolved in DMF (400 ml) and while stirring. DIC (34 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times). The above resin was deblocked with 400 ml of 20% piperidine in DMF for 10 min and 15 min and washed with one bed volume of DMF (2 times), IPA (2 times) and DMF (2 times).

Step D

Fmoc-Ala-OH (44.3 gm, 2 eq.) and HOBT (20 gm, 2 eq) were dissolved in DMF (400 ml) and while stirring. DIC (34 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times). The above resin was deblocked with 400 ml of 20% piperidine in DMF for 10 and 15 minutes and washed with one bed volume of DMF (2 times), IPA (2 times) and DMF (2 times).

Step E

Boc-His (Trt)-OH (73 gm, 2 eq.) and HOST (20 gm, 2 eq) were dissolved in DMF (500 ml) and while stirring DIC (34 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times), DCM (2 times) and MTBE (2 times). It was isolated and dried to give Boc-His (Trt)-Ala-Glu (Otbu)-Gly-CTC Resin.

Yield: 110 gm

Step F

Selective cleavage of 2-chloro trityl resin from the Boc-His (Trt)-Ala-Glu (Otbu)-Gly-CTC Resin was performed with a mixture 1% TFA in dichloromethane. The above peptidyl resin was taken in SPPS reactor and treated with a solution of 1% TFA in DCM for 5 minutes at room temp and drained. The filtrate was immediately neutralized with 15% DIEA in DCM under cooling. The above procedure was repeated twice to cleave the peptide from the resin completely. The dichloromethane solution was washed with water (2 times), organic layer was dried and concentrated under reduced pressure. Crude protected peptide was isolated by precipitating with MTBE Yield: 50 gm
Purity: 87.5%

Example 2

Synthesis of Fmoc-Thr(tbu)-Phe-Thr(tbu)-Ser(tbu)-Asp(Otbu)-Val-Ser(tbu)-Ser(tbu)-Tyr(tbu)-Leu-Glu(Otbu)-Gly-Gln(Trt)-Ala-Ala-Lys(Dde)-Glu(Otbu)-Phe-Ile-Ala-Trp(Boc)-Leu-Val-Arg(pbf)-Gly-Arg(pbf)-Gly-CTC Resin (Fragment A)

Step A

CTC resin (40 gm) was taken in a SPPS reactor, 300 ml of dry dichloromethane was added and allowed it to swell for 10 minutes and drained.

Step B

A solution of Fmoc-Gly-OH (8.3 gm, 0.7 eq) and DIEA (32 ml, 3 eq) in dry dichloromethane (300 ml) was added to the resin at step A and stirred for four hours at room temperature and drained. The resin was then capped with 400 ml of DIEA (1%) solution in DCM: Methanol (1:1)) for 20 min and drained. Thereafter, washed the resin with one bed volume of DMF (2 times), DCM (2 times) and MTBE (2 times) isolated and dried.

Yield: 46 gm
Loading ~0.5 mmol/g

The above resin was deblocked with 400 ml of 20% piperidine in DMF for 10 and 15 minutes and washed with 400 ml of DMF (2 time), IPA (2 times) and DMF (2 times).

Step C

Fmoc-Arg (pbf)-OH (30 gm, 2 eq.) and HOBT (6.2 gm, 2 eq) were dissolved in DMF (400 ml) and while stirring DIC (11 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times).

The repeated cycles of operations (Fmoc Deprotections and Amino acid couplings) were performed sequentially for Fmoc-Gly-OH, Fmoc-Arg (pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(Otbu)-OH, Fmoc-Lys(Dde)-OH, Fmoc-Ala-OH, Fmoc-Ala-OH, Fmoc-Gln(Trt)-OH, Fmoc-Gly-OH, Fmoc-Glu(Otbu)-OH, Fmoc-Leu-OH, Fmoc-Tyr (tbu)-OH, Fmoc-Ser (tbu)-OH, Fmoc-Ser (tbu)-OH, Fmoc-Val-OH, Fmoc-Asp (Otbu)-OH, Fmoc-Ser (tbu)-OH, Fmoc-Thr (tbu)-OH, Fmoc-Phe-OH, Fmoc-Thr (tbu)-OH until the desired peptidyl resin was obtained.

Example 3

Synthesis of Boc-His(Trt)-Ala-Glu(Otbu)-Gly-Thr(tbu)-Phe-Thr(tbu)-Ser(tbu)-Asp(Otbu)-Val-Ser(tbu)-Ser(tbu)-Tyr(tbu)-Leu-Glu(Otbu)-Gly-Gln(Trt)-Ala-Ala-Lys(Dde)-Glu(Otbu)-Phe-Ile-Ala-Trp(Boc)-Leu-Val-Arg(pbf)-Gly-Arg(pbf)-Gly-CTC Resin (Liraglutide precursor peptide on solid support)

Boc-His(Trt)-Ala-Glu(Otbu)-Gly-OH (37 gm, 2.0 eq) and HOBT (6.2 gm, 2 eq) were dissolved in DMF (500 ml) and while stirring DIC (11 ml, 3 eq) was added and stirred the reaction mixture for 5 min. It was added to the above peptidyl resin (Example 2) and stirred for six hours at room temperature. The progress of coupling was monitored by Kaiser Tests. After completion of the reaction the resin was drained and washed with one bed volume of DMF (2 times), DCM (2 times) and MTBE (2 times) isolated and dried to give desired product.

Example 4

```
Synthesis of Boc-His(Trt)-Ala-Glu(Otbu)-Gly-
Thr(tbu)-Phe-Thr(tbu)-Ser(tbu)-Asp(Otbu)-Val-
Ser(tbu)-Ser(tbu)-Tyr(tbu)-Leu-Glu(Otbu)-Gly-
Gln(Trt)-Ala-Ala-Lys(NαPalmitoyl-L-y-glu(X))-
Glu(Otbu)-Phe-Ile-Ala-Trp(Boc)-Leu-Val-Arg(pbf)-
Gly-Arg(pbf)-Gly-CTC Resin (Protected
Liraglutide on resin)
```

To the Peptidyl resin (example 3) was added 2% hydrazine hydrate in DMF and stirred for 20 minutes to deprotect Dde group of Lys at 20 positions. Fmoc-Glu-Otbu (19.6 gm, 2 eq) and HOBT (6.2 gm, 2 eq) were dissolved in DMF (500 ml) and while stirring. DIC (11 ml, 3 eq) was added and stirred the reaction mixture for 5 min. It was added to the above peptidyl resin and stirred for three hours at room temperature. The progress of coupling was monitored by Kaiser Tests. After completion of the reaction the resin was drained and washed with one bed volume of DMF (2 times). The above resin was deblocked with 600 ml of 20% piperidine in DMF for 10 and 15 minutes and washed with one bed volume of DMF (2 times), IPA (2 times) and DMF (2 times).

Palmitic acid (12 gm, 2 eq) and HOBT (6.2 gm, 2 eq) were dissolved in DMF (600 ml) and while stirring. DIC (11 ml, 3 eq) was added and stirred the reaction mixture for 5 min. It was added to the above peptidyl resin and stirred for three hours at room temperature. The progress of coupling was monitored by Kaiser Tests. After completion of the reaction the resin was drained and washed with one bed volume of DMF (2 times). DCM (2 times) and MTBE (2 times) isolated and dried to give desired product.

Yield: 107 gm

Example 5

Preparation of Crude Liraglutide

Deblocking of protected Liraglutide was performed with a mixture TFA+Water+TIS (90%+5%+5%) for 2 hrs at room temp. The crude peptide (Liraglutide) was isolated by precipitating with MTBE.

Yield: 41 gm Purity: 48%

Example 6

Purification of Liraglutide

Crude Liraglutide was purified by reverse phase C-18 HPLC using 0.1% aqueous triflouroacetic acid (as buffer A) and 100% acetonitrile (as buffer B). The fractions containing >95% pure Liraglutide triflouro acetate were pooled; the organic modifier was removed under reduced pressure. Desalting and second purification was performed with 0.01M ammonium bicarbonate (as buffer A) and 100% acetonitrile (as buffer B). The fractions containing pure Liraglutide were pooled; the organic modifier was removed under reduced pressure. The resulting peptide solution was freeze-dried to isolate white fluffy material as Liraglutide.

Yield: 2.0 gm
Purity: 99.4%

Example 7

```
Synthesis of Fmoc-Ser(tbu)-Tyr(tbu)-Leu-
Glu(Otbu)-Gly-OH (Fragment D)
```

Step A

CTC resin (50 gm) was taken in a SPPS reactor, 500 ml of dry dichloromethane was added and allowed it to swell for 10 minutes and drained.

Step B

A solution of Fmoc-Gly-OH (45 gm, 2 eq) and DIEA (39.5 ml, 3 eq) in dry dichloromethane (500 ml) was added to the resin at step A and stirred for one to two hours at room temperature and drained. The resin was then capped with 400 ml of DIEA (1%) solution in DCM: Methanol (1:1)) for 20 min and drained. Thereafter, washed the resin with one bed volume of DMF (2 times), DCM (2 times) and MTBE (2 times) isolated and dried.

Yield: 76 gm

Loading ~0.90

The above resin was deblocked with 500 ml of 20% piperidine in DMF for 10 and 15 minutes and washed with 400 ml of DMF (2 times), IPA (2 times) and DMF (2 times).

Step C

Fmoc-Glu (Otbu)-OH (59 gm, 2 eq.) and HOBT (19 gm, 2 eq) were dissolved in DMF (400 ml) and while stirring. DIC (32 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times). The above resin was deblocked with 400 ml of 20% piperidine in DMF for 10 min and 15 min and washed with one bed volume of DMF (2 times), IPA (2 times) and DMF (2 times).

Step D

Fmoc-Leu-OH (49 gm, 2 eq.) and HOBT (19 gm, 2 eq) were dissolved in DMF (400 ml) and while stirring. DIC (32 ml, 3 eq) was added and stirred the reaction mixture for 5 min. It was added to the resin in Step A and stirred for two to three hours at room temperature.

The progress of coupling was monitored by Kaiser Tests. After completion of the reaction the resin was drained and washed with one bed volume of DMF (2 times).

The above resin was deblocked with 400 ml of 20% piperidine in DMF for 10 and 15 minutes and washed with one bed volume of DMF (2 times), IPA (2 times) and DMF (2 times).

Step E

Fmoc-Tyr (tbu)-OH (64 gm, 2 eq.) and HOBT (19 gm, 2 eq) were dissolved in DMF (500 ml) and while stirring DIC (32 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times), DCM (2 times) and MTBE (2 times).

Step F

Fmoc-Ser (tbu)-OH (53 gm, 2 eq.) and HOBT (19 gm, 2 eq) were dissolved in DMF (500 ml) and while stirring DIC (32 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times), DCM (2 times) and MTBE (2 times). It was isolated and dried to give Fmoc-Ser (tbu)-Tyr (tbu)-Leu-Glu (Otbu)-Gly-CTC Resin.

Yield: 125 gm Step G

Selective cleavage of 2-chloro trityl resin from the Fmoc-Ser (tbu)-Tyr (tbu)-Leu-Glu (Otbu)-Gly-CTC Resin was performed with a mixture 1% TFA in dichloromethane.

The above peptidyl resin was taken in SPPS reactor and treated with a solution of 1% TFA in DCM for 5 minutes at room temp and drained. The filtrate was immediately neutralized with 15% DIEA in DCM under cooling. The above procedure was repeated twice to cleave the peptide from the resin completely. The dichloromethane solution was washed with water (2 times), organic layer was dried and concentrated under reduced pressure. Crude protected peptide was isolated by precipitating with MTBE Yield: 55 gm
Purity: 95.2%

Example 8

Synthesis of Fmoc-Gln(Trt)-Ala-Ala-Lys(Dde)-

Glu(Otbu)-Phe-Ile-Ala-Trp(Boc)-Leu-Val-Arg(pbf)-

Gly-Arg(pbf)-Gly-CTC Resin (Fragment C)

Step A

CTC resin (10 gm) was taken in a SPPS reactor, 300 ml of dry dichloromethane was added and allowed it to swell for 10 minutes and drained.

Step B

A solution of Fmoc-Gly-OH (2.0 gm, 0.7 eq) and DIEA (7.8 ml, 3 eq) in dry dichloromethane (100 ml) was added to the resin at step A and stirred for four hours at room temperature and drained. The resin was then capped with 100 ml of DIEA (1%) solution in DCM: Methanol (1:1)) for 20 min and drained. Thereafter, washed the resin with one bed volume of DMF (2 times), DCM (2 times) and MTBE (2 times) isolated and dried.

Yield: 11.5 gm
Loading ~0.5 mmol/g

The above resin was deblocked with 100 ml of 20% piperidine in DMF for 10 and 15 minutes and washed with 100 ml of DMF (2 time), IPA (2 times) and DMF (2 times).

Step C

Fmoc-Arg (pbf)-OH (7.5 gm, 2 eq.) and HOBT (1.6 gm, 2 eq) were dissolved in DMF (100 ml) and while stirring DIC (2.7 ml, 3 eq) was added and stirred the reaction mixture for 5 min. It was added to the resin in Step A and stirred for two to three hours at room temperature. The progress of coupling was monitored by Kaiser Tests. After completion of the reaction the resin was drained and washed with one bed volume of DMF (2 times).

The repeated cycles of operations (Fmoc Deprotections and Amino acid couplings) were performed sequentially for Fmoc-Gly-OH, Fmoc-Arg (pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(Otbu)-OH, Fmoc-Lys(Dde)-OH, Fmoc-Ala-OH, Fmoc-Ala-OH, Fmoc-Gln(Trt)-OH until the desired peptidyl resin was obtained.

Example 9

Synthesis of Fmoc-Thr(tbu)-Phe-Thr(tbu)-

Ser(tbu)-Asp(Otbu)-Val-Ser(tbu)-Ser(tbu)-

Tyr(tbu)-Leu-Glu(Otbu)-Gly-Gln(Trt)-Ala-Ala-

Lys(Dde)-Glu(Otbu)-Phe-Ile-Ala-Trp(Boc)-Leu-

Val-Arg(pbf)-Gly-Arg(pbf)-Gly-CTC Resin (Fragment A)

Step-A

Synthesis of Fmoc-Ser(tbu)-Tyr(tbu)-Leu-

Glu(Otbu)-Gly-Gln(Trt)-Ala-Ala-Lys(Dde)-

Glu(Otbu)-Phe-Ile-Ala-Trp(Boc)-Leu-Val-

Arg(pbf)-Gly-Arg(pbf)-Gly-CTC Resin

The above peptidyl resin (Example 8) was deblocked with 100 ml of 20% piperidine in DMF for 10 and 15 minutes and washed with one bed volume of DMF (2 times), WA (2 times) and DMF (2 times).

Fmoc-Ser (tbu)-Tyr(tbu)-Leu-Glu (Otbu)-Gly-OH (11 gm, 2.0 eq) and HOBT (1.6 gm, 2 eq) were dissolved in DMF (150 ml) and while stirring DIC (2.7 ml, 3 eq) was added and stirred the reaction mixture for 5 min. It was added to the peptidyl resin and stirred for six hours at room temperature. The progress of coupling was monitored by Kaiser Tests. After completion of the reaction the resin was drained and washed with one bed volume of DMF (2 times), DCM (2 times) and MTBE (2 times) isolated and dried to give desired product. The above peptidyl resin (Example 9) was deblocked with 100 ml of 20% piperidine in DMF for 10 and 15 minutes and washed with one bed volume of DMF (2 times), IPA (2 times) and DMF (2 times).

Step-B

Fmoc-Ser (tbu)-OH (4.4 gm, 2.0 eq) and HOBT (1.62 gm, 2 eq) were dissolved in DMF (150 ml) and while stirring DIC (2.7 ml, 3 eq) was added and stirred the reaction mixture for 5 min. It was added to the peptidyl resin and stirred for three hours at room temperature. The progress of coupling was monitored by Kaiser Tests. After completion of the reaction the resin was drained and washed with one bed volume of DMF (2 times), DCM (2 times) and MTBE (2 times) isolated and dried to give desired product. The repeated cycles of operations (Fmoc Deprotections and Amino acid couplings) were performed sequentially for Fmoc-Val-OH, Fmoc-Asp(Otbu)-OH, Fmoc-Ser(tbu)-OH, Fmoc-Thr(tbu)-OH, Fmoc-Phe-OH, Fmoc-Thr(tbu)-OH until the desired peptidyl resin was obtained.

Example 10

```
Synthesis of Boc-His(Trt)-Ala-Glu(Otbu)-Gly-
Thr(tbu)-Phe-Thr(tbu)-Ser(tbu)-Asp(Otbu)-Val-
Ser(tbu)-Ser(tbu)-Tyr(tbu)-Leu-Glu(Otbu)-Gly-
Gln(Trt)-Ala-Ala-Lys(Dde)-Glu(Otbu)-Phe-Ile-Ala-
Trp(Boc)-Leu-Val-Arg(pbf)-Gly-Arg(pbf)-Gly-CTC
Resin (Liraglutide precursor peptide on solid
support)
```

The above peptidyl resin (Example 9) was deblocked with 100 ml of 20% piperidine in DMF for 10 and 15 minutes and washed with one bed volume of DMF (2 times), IPA (2 times) and DMF (2 times).

Boc-His(Trt)-Ala-Glu(Otbu)-Gly-OH (9.3 gm, 2.0 eq) and HOBT (1.6 gm, 2 eq) were dissolved in DMF (150 ml) and while stirring DIC (2.7 ml, 3 eq) was added and stirred the reaction mixture for 5 min. It was added to the peptidyl resin and stirred for six hours at room temperature. The progress of coupling was monitored by Kaiser Tests. After completion of the reaction the resin was drained and washed with one bed volume of DMF (2 times), DCM (2 times) and MTBE (2 times) isolated and dried to give desired product

Example 11

```
Synthesis of Boc-His(Trt)-Ala-Glu(Otbu)-Gly-
Thr(tbu)-Phe-Thr(tbu)-Ser(tbu)-Asp(Otbu)-Val-
Ser(tbu)-Ser(tbu)-Tyr(tbu)-Leu-Glu(Otbu)-Gly-
Gln(Trt)-Ala-Ala-Lys(NαPalmitoyl-L-γ-glu(X))-
Glu(Otbu)-Phe-Ile-Ala-Trp(Boc)-Leu-Val-
Arg(pbf)-Gly-Arg(pbf)-Gly-CTC Resin
(Protected Liraglutide on resin)
```

To the Peptidyl resin (example 10) was added 2% hydrazine hydrate in DMF and stirred for 20 minutes to deprotect Dde group of Lys at 20 positions.

Fmoc-Glu-Otbu (4.9 gm, 2 eq) and HOBT (1.6 gm, 2 eq) were dissolved in DMF (150 ml) and while stirring. DIC (2.7 ml, 3 eq) was added and stirred the reaction mixture for 5 min. It was added to the above peptidyl resin and stirred for three hours at room temperature. The progress of coupling was monitored by Kaiser Tests. After completion of the reaction the resin was drained and washed with one bed volume of DMF (2 times). The above resin was deblocked with 100 ml of 20% piperidine in DMF for 10 and 15 minutes and washed with one bed volume of DMF (2 times), IPA (2 times) and DMF (2 times).

Palmitic acid (3 gm, 2 eq) and HOBT (1.6 gm, 2 eq) were dissolved in DMF (150 ml) and while stirring. DIC (2.7 ml, 3 eq) was added and stirred the reaction mixture for 5 min. It was added to the above peptidyl resin and stirred for three hours at room temperature. The progress of coupling was monitored by Kaiser Tests. After completion of the reaction the resin was drained and washed with one bed volume of DMF (2 times). DCM (2 times) and MTBE (2 times) isolated and dried to give desired product.

Yield: 25 gm

Example 12

Preparation of Crude Liraglutide

Deblocking of protected Liraglutide was performed with a mixture TFA+Water+TIS (90%+5%+5%) for 2 hrs at room temp. The crude peptide (Liraglutide) was isolated by precipitating with MTBE.

Yield: 10 gm
Purity: 50.8%

Example 13

Purification of Liraglutide

Crude Liraglutide was purified by reverse phase C-18 HPLC using 0.1% aqueous triflouroacetic acid (as buffer A) and 100% acetonitrile (as buffer B).

The fractions containing >95% pure Liraglutide triflouro acetate were pooled; the organic modifier was removed under reduced pressure. Desalting and second purification was performed with 0.01M ammonium bicarbonate (as buffer A) and 100% acetonitrile (as buffer B). The fractions containing pure Liraglutide were pooled; the organic modifier was removed under reduced pressure. The resulting peptide solution was freeze-dried to isolate white fluffy material as Liraglutide.

Yield: 0.4 gm
Purity: >99%.

---

We claim:

1. A process for the preparation of Liraglutide of Formula I,

FORMULA I

His-Ala-Glu-Gly-Thr-Phe-Thr-Ser-Asp-Val-Ser-Ser-Tyr-Leu-Glu-
  Palmitoyl-Glu-γ
  |
-Gly-Gln-Ala-Ala-Lys-Glu-Phe-Ile-Ala-Trp-Leu-Val-Arg-Gly-Arg-Gly-OH comprising the following steps:
a) preparing Fragment A (SEQ ID NO: 7)
Y-Thr(X)-Phe-Thr(X)-Ser(X)-Asp(X)-Val-Ser(X)-

Ser(X)-Tyr(X)-Leu-Glu(X)-Gly-Gln(Trt)-Ala-Ala-

Lys-ϵ(P)-Glu(X)-Phe-Ile-Ala-Trp(X)-Leu-Val-

Arg(Z)-Gly-Arg(Z)-Gly-Resin (SEQ ID NO: 7) wherein,
Y represents amino protecting group,
X represents carboxyl, phenol or alcoholic protecting group,
Z represents guanidine protecting group and
P represents amino protecting group of -amino group of Lys by a solid phase synthesis,
b) coupling of Fragment A and Fragment B Boc-His(Trt)-Ala-Glu(X)-Gly-OH (SEQ ID NO: 8) by a solid phase synthesis to obtain Liraglutide precursor peptide on solid support,
c) modifying the Liraglutide precursor peptide on solid support at ϵ amino group of Lys to obtain protected Liraglutide,
d) concurrently cleaving the protected peptide from the solid support and deprotecting the peptide,
e) purification of Liraglutide (crude) on reverse phase HPLC,
f) isolating pure Liraglutide.

2. The process according to claim 1, wherein the Fragment A is prepared by the following steps
a) preparing fragment C Y-Gln(Trt)-Ala-Ala-Lys-ϵ(P)-Glu(X)-Phe-Ile-Ala-Trp(X)-Leu-Val-Arg(Z)-Gly-Arg(Z)-Gly-Resin (SEQ ID NO: 9) by a solid phase synthesis,
b) converting Fragment C to Fragment A by coupling with Fragment D Y-Ser(X)-Tyr(X)-Leu-Glu(X)-Gly-OH (SEQ ID NO: 10) and sequential addition of required amino acids by a solid phase synthesis.

3. The process according to claim 1 wherein the Fragment A is prepared by sequential addition of corresponding amino acids using a solid phase.

4. The process according to claim 1 wherein the Fragment B is prepared by sequential addition of corresponding amino acids using a solid phase.

5. The process according to claim 2 wherein the Fragment C is prepared by sequential addition of corresponding amino acids using a solid phase.

6. The process according to claim 2 wherein the Fragment D is prepared by sequential addition of corresponding amino acids using a solid phase.

7. The process according to claim 1, wherein the coupling is carried out in the presence of coupling agent(s).

8. The coupling agent (s) according to claim 7, is selected from the group comprising of hydroxybenzotriazole (HOBt), O-(7-azabenzotriazol-1-yl)-1,1,3,3-tetramethyluronium hexafluorophosphate (HATU), O-(benzotriazol-1-yl)-N,N,N'N'-tetramethyluronium tetrafluoroborate (TBTU), 1,3-dicyclohexylcarboimide (DCC), 1-(dimethylaminopropyl)-3-ethylcarbodiimide hydrochloride (EDC HCL), didisopropylcarbodiimide (DIC), isopropylchloroformate (IPCF), O-(benzotriazol-1-yl)-1,1,3,3-tetramethyluronium hexafluorophosphate (HBTU), benzotriazol 1-yl-oxy-tris (dimethyl-amino)-phosphonium hexafluorophaosphate (BOP), N,N-bis-(2-oxo-3-oxaolidinyl)phosphonic dichloride (BOP—Cl), benzotriazol-1-yloxytri(pyrrolidino)phosphonium hexafluorophosphate (PyBOP), chlorotri(pyrrolidino)phosphonium hexafluorophosphate (PyClOP), ethylecyano-2-(hydroxyimino) acetate (Oxyma Pure), O-(6-Chloro-1-nydrocibenzotriazol-1-yl)-1,1,3,3-tetramethyl uranium tetrafluoroborate (TCTU), 2-(5-norbornen-2,3-dicarboximido)-1,1,3,3-tetramethyluronium tetrafluoroborate (TNTU), propane phosphonic acid anhydride (PPAA), 2 succinimido-1,1,3,3-tetramethyluroniumtetrafluoroborate (TSTU), bromo-tris-pyrrolidino-phosphonium hexafluorophosphate (PyBroP), iso-butylchloroformate (IBCF), Ethyl 1,2-dihydro-2-ethoxyquinoline-1-carboxylate (EEDQ), 1-Cyano-2-ethoxy-2-0x0ehtylidenaminooxy)dimethyl-amino-morpholino-carbenium hexaflurorphosphate (COMU), 3-(diethoxyphosphoryloxy)-1,2,3-benzotriazin-4 (3H)-one (DEPBT) or mixtures thereof.

9. The process according to claim 1 wherein the coupling talks place in the presence of a solvent selected from the group comprising of DMF, DCM, THF, NMP, DMAC, methanol, ethanol, isopropanol, dichloroethane, 1,4-dioxane, 2-methyl tetrahydrofuran ethyl acetate, acetonitrile, acetone, or mixtures thereof.

10. The process according to claim 1, wherein the coupling is carried out in presence of a base.

11. The process according to claim 10 wherein the base is organic base or inorganic base.

12. The process according to claim 11, wherein the organic base is selected from the group comprising of potassium carbonate, lithium carbonate, sodium carbonate, sodium ethoxide, sodium bicarbonate, potassium bicarbonate, sodium hydroxide, potassium hydroxide, ammonium hydroxide, and mixtures thereof.

13. The process according to claim 11, wherein the organic base is selected from the group comprising of diisopropylamine, N,N-diisopropylethylamine, trimethylamine, dimethylamine, isopropyl ethylamine, pyridine, N-methyl morpholine and mixtures thereof.

14. The process according to claim 1, wherein the deprotection of peptide is carried out using a mixture of reagents selected from the group comprising TFS, TIS, DTT, EDT, ammonium iodide, 2,2'-(ethylenedioxy)diethane, acetyl cysteine, DMS, phenol, cresol and thiocresol.

15. The process according to claim 1, wherein the final isolation of the Liraglutide is carried out by lypophilization.

\* \* \* \* \*

SEQUENCE LISTING

```
<160> NUMBER OF SEQ ID NOS: 10

<210> SEQ ID NO 1
<211> LENGTH: 31
<212> TYPE: PRT
<213> ORGANISM: Artificial Sequence
<220> FEATURE:
<223> OTHER INFORMATION: Liraglutide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

<210> SEQ ID NO 2
<211> LENGTH: 27
<212> TYPE: PRT
<213> ORGANISM: Artificial Sequence
<220> FEATURE:
<223> OTHER INFORMATION: Synthetic

<400> SEQUENCE: 2

Thr Phe Thr Ser Asp Val Ser Ser Tyr Leu Glu Gly Gln Ala Ala Lys
1               5                   10                  15

Glu Phe Ile Ala Trp Leu Val Arg Gly Arg Gly
            20                  25

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

His Ala Glu Gly
1

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Gln Ala Ala Lys Glu Phe Ile Ala Trp Leu Val Arg Gly Arg Gly
1               5                   10                  15

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Ser Tyr Leu Glu Gly
1               5

<210> SEQ ID NO 6
<211> LENGTH: 31
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (20)..(20)
<223> OTHER INFORMATION: Lys 20 linked to Palmitoyl-Glu-y
<220> FEATURE:
<221> NAME/KEY: misc_feature
<222> LOCATION: (31)..(31)
<223> OTHER INFORMATION: C-term OH

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

```
<210> SEQ ID NO 7
<211> LENGTH: 27
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Thr linked to amino protecting group
<220> FEATURE:
<221> NAME/KEY: misc_feature
<222> LOCATION: (1)..(1)
<223> OTHER INFORMATION: Thr linked to another protecting group
<220> FEATURE:
<221> NAME/KEY: misc_feature
<222> LOCATION: (3)..(3)
<223> OTHER INFORMATION: Thr linked to a protecting group
<220> FEATURE:
<221> NAME/KEY: misc_feature
<222> LOCATION: (4)..(4)
<223> OTHER INFORMATION: Ser linked to a protecting group
<220> FEATURE:
<221> NAME/KEY: misc_feature
<222> LOCATION: (5)..(5)
<223> OTHER INFORMATION: Asp linked to a protecting group
<220> FEATURE:
<221> NAME/KEY: misc_feature
<222> LOCATION: (7)..(7)
<223> OTHER INFORMATION: Ser linked to a protecting group
<220> FEATURE:
<221> NAME/KEY: misc_feature
<222> LOCATION: (8)..(8)
<223> OTHER INFORMATION: Ser linked to a protecting group
<220> FEATURE:
<221> NAME/KEY: misc_feature
<222> LOCATION: (9)..(9)
<223> OTHER INFORMATION: Tyr linked to a protecting group
<220> FEATURE:
<221> NAME/KEY: misc_feature
<222> LOCATION: (11)..(11)
<223> OTHER INFORMATION: Glu linked to a protecting group
<220> FEATURE:
<221> NAME/KEY: misc_feature
<222> LOCATION: (13)..(13)
<223> OTHER INFORMATION: Gln linked to a protecting group Trt
<220> FEATURE:
<221> NAME/KEY: misc_feature
<222> LOCATION: (16)..(16)
<223> OTHER INFORMATION: Lys linked to amino protecting group
<220> FEATURE:
<221> NAME/KEY: misc_feature
<222> LOCATION: (17)..(17)
<223> OTHER INFORMATION: Glu linked to a protecting group
<220> FEATURE:
<221> NAME/KEY: misc_feature
<222> LOCATION: (21)..(21)
<223> OTHER INFORMATION: Trp linked to a protecting group
<220> FEATURE:
<221> NAME/KEY: misc_feature
<222> LOCATION: (24)..(24)
<223> OTHER INFORMATION: Arg linked to a protecting group
<220> FEATURE:
<221> NAME/KEY: misc_feature
<222> LOCATION: (26)..(26)
<223> OTHER INFORMATION: Arg linked to a protecting group
<220> FEATURE:
<221> NAME/KEY: misc_feature
<222> LOCATION: (27)..(27)
<223> OTHER INFORMATION: Gly linked to a resin

<400> SEQUENCE: 7

Thr Phe Thr Ser Asp Val Ser Ser Tyr Leu Glu Gly Gln Ala Ala Lys
1               5                   10                  15

Glu Phe Ile Ala Trp Leu Val Arg Gly Arg Gly
            20                  25
```

```
<210> SEQ ID NO 8
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: the amino group of His protected by Boc and
      side chain protected by Trt
<220> FEATURE:
<221> NAME/KEY: misc_feature
<222> LOCATION: (3)..(3)
<223> OTHER INFORMATION: Glu linked to a protecting group
<220> FEATURE:
<221> NAME/KEY: misc_feature
<222> LOCATION: (4)..(4)
<223> OTHER INFORMATION: Gly  C-Term OH

<400> SEQUENCE: 8

His Ala Glu Gly
1

<210> SEQ ID NO 9
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Gln with amino protecting group and side chain
      protected by Trt
<220> FEATURE:
<221> NAME/KEY: misc_feature
<222> LOCATION: (4)..(4)
<223> OTHER INFORMATION: Lys linked to amino protecting group
<220> FEATURE:
<221> NAME/KEY: misc_feature
<222> LOCATION: (5)..(5)
<223> OTHER INFORMATION: Glu linked to a protecting group
<220> FEATURE:
<221> NAME/KEY: misc_feature
<222> LOCATION: (9)..(9)
<223> OTHER INFORMATION: Trp linked to a protecting group
<220> FEATURE:
<221> NAME/KEY: misc_feature
<222> LOCATION: (12)..(12)
<223> OTHER INFORMATION: Arg linked to a protecting group
<220> FEATURE:
<221> NAME/KEY: misc_feature
<222> LOCATION: (14)..(14)
<223> OTHER INFORMATION: Arg linked to a protecting group
<220> FEATURE:
<221> NAME/KEY: misc_feature
<222> LOCATION: (15)..(15)
<223> OTHER INFORMATION: Gly linked to a resin

<400> SEQUENCE: 9

Gln Ala Ala Lys Glu Phe Ile Ala Trp Leu Val Arg Gly Arg Gly
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
```

```
<223> OTHER INFORMATION: Ser linked to amino protecting group and side
      chain linked to a protecting group
<220> FEATURE:
<221> NAME/KEY: misc_feature
<222> LOCATION: (2)..(2)
<223> OTHER INFORMATION: Tyr linked to a protecting group
<220> FEATURE:
<221> NAME/KEY: misc_feature
<222> LOCATION: (4)..(4)
<223> OTHER INFORMATION: Glu linked to a protecting group
<220> FEATURE:
<221> NAME/KEY: misc_feature
<222> LOCATION: (5)..(5)
<223> OTHER INFORMATION: Gly C-term OH

<400> SEQUENCE: 10

Ser Tyr Leu Glu Gly
1               5
```